United States Patent [19]

Barcza

[11] 4,208,408
[45] Jun. 17, 1980

[54] SUBSTITUTED 1-OXA-4-AZA-2,6-DISILACYCLOHEXANES

[75] Inventor: Sandor Barcza, West Orange, N.J.

[73] Assignee: Sandoz, Inc., E. Hanover, N.J.

[21] Appl. No.: 965,021

[22] Filed: Nov. 30, 1978

Related U.S. Application Data

[63] Continuation-in-part of Ser. No. 957,551, Nov. 3, 1978, abandoned, which is a continuation of Ser. No. 883,886, Mar. 6, 1978, abandoned.

[51] Int. Cl.$^2$ .............................................. C07F 7/10
[52] U.S. Cl. ..................................... 424/184; 556/408
[58] Field of Search ................. 424/184; 260/448.2 N

[56] References Cited

U.S. PATENT DOCUMENTS

| | | | |
|---|---|---|---|
| 3,159,661 | 12/1964 | Jones et al. ................. | 260/448.2 N |
| 3,448,137 | 6/1969 | Niederprüm et al. ..... | 260/448.2 N X |
| 4,132,725 | 1/1979 | Barcza ........................ | 260/448.2 N |

Primary Examiner—Paul F. Shaver
Attorney, Agent, or Firm—Gerald D. Sharkin; Robert S. Honor; Timothy G. Rothwell

[57] ABSTRACT

This disclosure describes novel compounds of the formula:

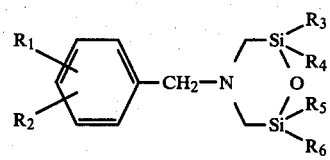

where
$R_1$ and $R_2$ each independently represent hydrogen, halo having an atomic weight of about 19 to 36, lower alkyl, lower alkoxy, trifluoromethyl or $R_1$ is

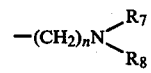

and $R_2$ is hydrogen,
wherein
$R_7$ and $R_8$ are each independently hydrogen or lower alkyl and
n is 0 or 1, and
$R_3$, $R_4$, $R_5$ and $R_6$ each independently represent lower alkyl, which are useful as muscle relaxants.

21 Claims, No Drawings

SUBSTITUTED 1-OXA-4-AZA-2,6-DISILACYCLOHEXANES

This application is a continuation-in-part of copending application Ser. No. 957,551, filed Nov. 3, 1978 now abandoned, which in turn is a continuation of Ser. No. 883,886, filed Mar. 6, 1978 now abandoned.

This invention relates to substituted 1-oxa-4-aza-2,6-disilacyclohexanes which exhibit muscle relaxant activity. In particular it relates to 2,2,6,6-tetramethyl-1-oxa-4-aza-2,6-disilacyclohexanes and pharmaceutically acceptable salts.

The compounds of this invention may be represented by the following structural formula

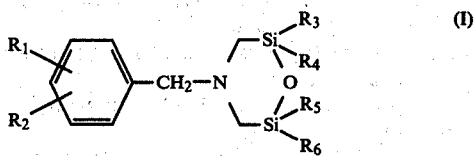

where
R$_1$ and R$_2$ each independently represent hydrogen, halo having an atomic weight of about 19 to 36, lower alkyl, i.e., lower alkyl having 1 to 4 carbon atoms, e.g., methyl, ethyl and the like, lower alkoxy, i.e., lower alkoxy having 1 to 4 carbon atoms, e.g., methoxy, ethoxy and the like, or trifluoromethyl, or R$_1$ is

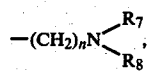

and R$_2$ is hydrogen,
wherein
R$_7$ and R$_8$ each independently represent hydrogen or lower alkyl having 1 to 2 carbon atoms, i.e., methyl or ethyl, and
n is 0, or 1, and
R$_3$, R$_4$, R$_5$ and R$_6$ each independently represent lower alkyl having 1 to 2 carbon atoms, i.e., methyl or ethyl.

The compounds of formula (I) are prepared according to the following reaction scheme:

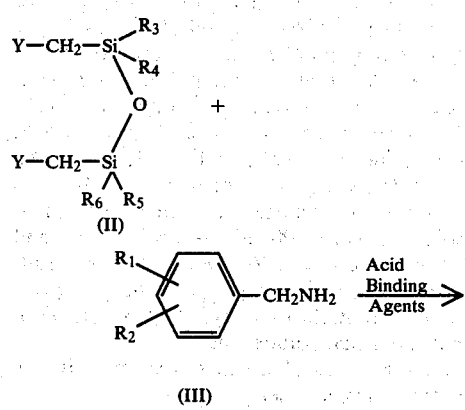

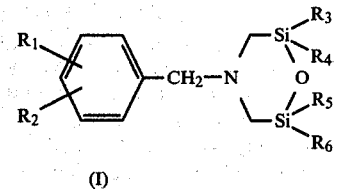

where
Y is a leaving group such as an arylsulfonate or alkylsulfonate, e.g., tosylate or mesylate or iodo, bromo chloro and the like, preferably iodo, and
R$_1$, R$_2$, R$_3$, R$_4$, R$_5$ and R$_6$ are as defined above.

The compounds of formula (I) are prepared by reacting a compound of the formula (II) with a compound of the formula (III) in the presence of an acid binding agent. Although the particular acid binding agent employed is not critical, the preferred acid binding agents include pyridine, triethylamine, diisopropylmethylamine, alkali metal hydroxides or hydrides such as potassium hydroxide, sodium hydroxide, lithium hydride and the like, or an excess of a compound of formula (III), the latter being especially preferred. It is preferred that the reaction be carried out without a solvent, however, aprotic solvents such as acetonitrile, dimethylformamide, dimethylacetamide, and the like and protic solvents such as the lower alkanols, e.g., methanol, ethanol and the like may be employed if the use of a solvent is desired. The temperature of the reaction is not critical, but it is preferred that the reaction be run from about −10° to 100° C., preferably from about 20° to 30° C. The reaction is run from about 2 to 12 hours, preferably from about 3 to 5 hours. The product is recovered using conventional techniques, e.g., filtration and evaporation followed by distillation.

Many of the compounds of formulae (II) and (III) are known and may be prepared by methods described in the literature. The compounds of formulae (II) and (III) not specifically described in the literature may be prepared by analogous methods from known starting materials.

The preferred compounds of formula (I) are the compounds wherein R$_3$, R$_4$, R$_5$ and R$_6$ each represent methyl. Particularly, preferred compounds are those in which R$_1$ is hydrogen, R$_2$ is hydrogen or m-methoxy and R$_3$, R$_4$, R$_5$ and R$_6$ each represent methyl.

The compounds of formula (I) are useful because they possess pharmacological activity in animals as muscle relaxants as indicated (1) by their activity in the rotorod test as described by Dunham and Miya (J. Am. Pharm. Assoc., 45: 208, 1957), (2) by their ability to depress spinal reflexes measured by flexor and patellar responses using force displacement transducers in male cats given 0.1 to 3.0 milligrams per kilogram of animal body weight, i.v. of the test compound, and (3) by their ability to produce docility in behavior tests in mice given 25 to 200 mg/kg of animal body weight, i.p. of the test compound according to the 30-word adjective check sheet system basically as described by Irwin S. (Gordon Research Conference, Medicinal Chemistry, 1959), and Chen (Symposium on Sedative and Hypnotic Drugs, Williams and Wilkins, 1954).

The muscle relaxant effective dosage of the compounds of formula (I) will vary depending upon the particular compound employed. However, in general, satisfactory results are obtained when the compounds are administered orally at a daily dosage of from about 1.0 milligram to about 100 milligrams per kilogram of animal body weight, typically given in divided doses two to four times per day. For most large mammals, the total daily dosage is from about 5 to about 500 milligrams and dosage forms suitable for internal administration comprise from about 1.25 to about 250 milligrams of the compound in admixture with a solid or liquid pharmaceutical carrier or diluent.

For the above-mentioned use, the compounds may be administered orally in such forms as tablets, capsules, elixirs, suspensions and the like or parenterally in the form of an injectable solutions or suspensions. The dosage will vary depending upon the mode of administration utilized and the compound employed.

The compounds of formula (I) may be similarly admininstered in the form of their non-toxic pharmaceutically acceptable salts. Such salts possess the same order of activity as the non-salt form and are readily prepared by reacting the molecule with an appropriate acid or an appropriate base by conventional technique, and, accordingly, are included within the scope of this invention. Representative of such salts are the mineral acid salts, e.g., hydrochloride, hydrobromide, sulfate and the like.

Tablets and capsules containing the ingredients indicated below may be useful as muscle relaxants, in divided doses two to four times per day.

| Ingredients | Weight (mg.) Tablet | Capsule |
|---|---|---|
| 4-benzyl-2,2,6,6-tetramethyl-1-oxa-4-aza-2,6-disilacyclohexane | 200 | 200 |
| tragacanth | 10 | — |
| lactose | 247.5 | 300 |
| corn starch | 25 | — |
| talcum | 15 | — |
| magnesium stearate | 2.5 | — |
| | 500 mg. | 500 mg. |

EXAMPLE 1

4-benzyl-2,2,6,6-tetramethyl-1-oxa-4-aza-2,6-disilacyclohexane.

An amount of 33.6 g. (0.315 mole) of benzylamine is added over a period of approximately 5 minutes to 41.4 g. (0.1 mole) of 1,3-bis-iodomethyl-1,1,3,3-tetramethyldisiloxane with stirring in a bath at room temperature. Stirring is continued at room temperature for one hour. (A slurry resulted). Addition of 50 ml. of acetonitrile gives a clear solution which is then heated to reflux for 2 hours. The cooled solution is distributed between approximately 0.5 l. of pentane and 1.5 l. of water. The aqueous layer is then extracted with one more approximately 200 ml. portion of pentane, and the combined organic layer is washed twice with approximately 300 ml. of water, dried over anhydrous sodium sulfate, filtered and evaporated in vacuo to provide a clear yellow mobile liquid. This product is then vacuum distilled to give 4-benzyl-2,2,6,6-tetramethyl-1-oxa-4-aza-2,6-disilacyclohexane; b.p. 134° to 135° C., at 13 mm Hg.

The hydrochloride salt of the title compound is prepared by dissolving 10.0 g (37.7 m moles) of the free base in 150 ml. of diethylether. There is then injected with stirring and ice-cooling 900 ml. of hydrogen chloride gas. The resulting slurry is allowed to stand at 0° overnight, filtered and the precipitate is washed with more ether and dried at 110° C. in vacuo to give the hydrochloride salt; m.p. 250° to 251° C.

Following the above procedure and using in place of benzylamine an equivalent amount of
(a) p-chlorobenzylamine,
(b) p-fluorobenzylamine,
(c) p-methylbenzylamine,
(d) p-methoxybenzylamine,
(e) 3,4-dichlorobenzylamine,
(f) m-trifluoromethylbenzylamine,
(g) p-dimethylaminobenzylamine,
(h) p-dimethylaminomethylbenzylamine
(i) m-chlorobenzylamine,
(j) m-methylbenzylamine, or
(k) o-chlorobenzylamine, there is obtained
(a) 4-(p-chlorobenzyl)-2,2,6,6-tetramethyl-1-oxa-4-aza-2,6-disilacyclohexane,
(b) 4-(p-fluorobenzyl)-2,2,6,6-tetramethyl-1-oxa-4-aza-2,6-disilacyclohexane,
(c) 4-(p-methylbenzyl)-2,2,6,6-tetramethyl-1-oxa-4-aza-2,6-disilacyclohexane,
(d) 4-(p-methoxybenzyl)-2,2,6,6-tetramethyl-1oxa-4-aza-2,6-disilacyclohexane,
(e) 4-(3,4-dichlorobenzyl)-2,2,6,6-tetramethyl-1-oxa-4-aza-2,6-disilacyclohexane,
(f) 4-(3-trifluoromethylbenzyl)-2,2,6,6-tetramethyl-1-oxa-4-aza-2,6-disilacyclohexane,
(g) 4-(4-dimethylaminobenzyl)-2,2,6,6-tetramethyl-1-oxa-4-aza-2,6-disilacyclohexane,
(h) 4-(4-dimethylaminomethylbenzyl)-2,2,6,6-tetramethyl-1-oxa-4-aza-2,6-disilacyclohexane,
(i) 4-(m-chlorobenzyl)-2,2,6,6-tetramethyl-1-oxa-4-aza-2,6-disilacyclohexane,
(j) 4-(m-methylbenzyl)-2,2,6,6-tetramethyl-1-oxa-4-aza-2,6-disilacyclohexane, or
(k) 4-(o-chlorobenzyl-2,2,6,6-tetramethyl-1-oxa-4-aza-2,6-disilacyclohexane, respectively.

The 4-benzyl-2,2,6,6-tetramethyl-1-oxa-4-aza-2,6-disilacyclohexane of this example is an effective muscle relaxant when orally administered to an animal in need of said treatment at a dosage of 100 mg. two to four times per day.

EXAMPLE 2

4-(m-methoxybenzyl)-2,2,6,6-tetramethyl-1-oxa-4-aza-2,6-disilacyclohexane.

A solution containing 92.4 g. (400 m moles) of 1,3-bis-chloromethyl-1,1,3,3-tetramethyldisiloxane and 100 g. of acetonitrile, dried over molecular sieves, is heated to 90° bath temperature. To this solution there is added with stirring a solution of 55 g. (400 m moles) of m-methoxybenzylamine in 88.8 g. (2×1.1×400=880 m moles) of triethylamine, over a period of 25 minutes. A solid separated in the reaction mixture from the time at which about half the amine is added. The mildly exothermic reaction kept the mixture refluxing. The resulting slurry is then stirred for an additional 4¾ hours then cooled in ice. Toluene (∼0.5 l) is then added and the mixture is extracted with 1 liter of water; the latter is washed with 100 ml. of toluene. The combined organic phase is washed with two 500 ml. portions of water and concentrated in vacuo first at 40° then at 60°. The resultant 118.7 g. of oil is distilled through a short Vigreux column to give 4-(m-methoxybenzyl)-2,2,6,6-tetramethyl-1-oxa-4-aza-2,6-disilacyclohexane.

The hydrochloride salt of the title compound is prepared in the following manner.

A solution of 13.5 ml. aqueous concentrated hydrochloric acid (slight excess over 135 m mol) in 50 ml. of acetone is added without cooling to a solution of 40 g. (135 m mol) of 4-(m-methoxybenzyl)-2,2,6,6-tetramethyl-1-oxa-4-aza-2,6-disilacyclohexane in 100 ml. of acetone. An additional 50 ml. of acetone is added to facilitate stirring. The resultant white slurry is stirred for 10 min., then 100 ml. of ethyl acetate is added, while continuing stirring for an additional 10 minutes. The mixture is then allowed to stand at 0° for 3 hours. The resulting slurry is then filtered and the precipitate is washed with 60 ml. of 1:1 acetone:ethyl acetate, then with 50 ml. of ethyl acetate, the solids are resuspended in each portion of wash. The resulting product is dried overnight in vacuo at 100° C. to give the hydrochloride salt; m.p. 230° to 231.5°.

What is claimed is:

1. A compound of the formula

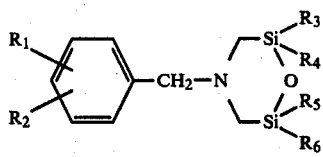

where
$R_1$ and $R_2$ each independently represent hydrogen, halo having an atomic weight of about 19 to 36, lower alkyl having 1 to 4 carbon atoms, lower alkoxy having 1 to 4 carbon atoms, trifluromethyl, or
$R_1$ is

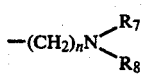

and $R_2$ is hydrogen,
wherein
$R_7$ and $R_8$ are each independently hydrogen or lower alkyl having 1 to 2 carbon atoms,
n is 0 or 1, and
$R_3$, $R_4$, $R_5$ and $R_6$ each independently represent lower alkyl having 1 to 2 carbon atoms or
a pharmaceutically acceptable salt thereof.
2. A compound of claim 1 in free base form.
3. A compound of claim 1 in the hydrochloride salt form.
4. A compound of claim 1 in which $R_3$, $R_4$, $R_5$ and $R_6$ are methyl.
5. A compound of claim 1 in which $R_1$ is hydrogen and $R_3$, $R_4$, $R_5$ and $R_6$ are methyl.
6. The compound of claim 1 which is 4-benzyl-2,2,6,6-tetramethyl-1-oxa-4-aza-2,6-disilacyclohexane.
7. The compound of claim 1 which is 4-benzyl-2,2,6,6-tetramethyl-1-oxa-4-aza-2,6-disilacyclohexane hydrochloride.
8. The compound of claim 1 which is 4-(p-fluorobenzyl)-2,2,6,6-tetramethyl-1-oxa-4-aza-2,6-disilacyclohexane.
9. The compound of claim 1 which is 4-(p-fluorobenzyl)-2,2,6,6-tetramethyl-1-oxa-4-aza-2,6-disilacyclohexane hydrochloride.
10. The compound of claim 1 which is 4-(p-methoxybenzyl)-2,2,6,6-tetramethyl-1-oxa-4-aza-2,6-disilacyclohexane.
11. The compound of claim 1 which is 4-(p-methoxybenzyl)-2,2,6,6-tetramethyl-1-oxa-4-aza-2,6-disilacyclohexane hydrochloride.
12. The compound of claim 1 which is 4-(m-methoxybenzyl)-2,2,6,6-tetramethyl-1-oxa-4-aza-2,6-disilacyclohexane.
13. The compound of claim 1 which is 4-(m-methoxybenzyl)-2,2,6,6-tetramethyl-1-oxa-4-aza-2,6-disilacyclohexane hydrochloride.
14. A method of treating muscle spasms which comprises administering to a mammal in need of said treatment a muscle relaxant effective amount of a compound according to claim 1.
15. A pharmaceutical composition for use as a muscle relaxant which comprises administering to a manual in need of said treatment a muscle relaxant effective amount of a compound of claim 1 and a pharmaceutically acceptable carrier therefor.
16. The compound of claim 1 which is 4-(p-methylbenzyl)-2,2,6,6-tetramethyl-1-oxa-4-aza-2,6-disilacyclohexane.
17. The compound of claim 1 which is 4-(3-trifluoromethylbenzyl)-2,2,6,6-tetramethyl-1-oxa-4-aza-2,6-disilacyclohexane.
18. The compound of claim 1 which is 4-(o-chlorobenzyl)-2,2,6,6-tetramethyl-1-oxa-4-aza-2,6-disilacyclohexane.
19. The compound of claim 1 which is 4-(m-methylbenzyl)-2,2,6,6-tetramethyl-1-oxa-4-aza-2,6-disilacyclohexane.
20. The compound of claim 1 which is 4-(m-chlorobenzyl)-2,2,6,6-tetramethyl-1-oxa-4-aza-2,6-disilacyclohexane.
21. The compound of claim 1 which is 4-(3,4-dichlorobenzyl)-2,2,6,6-tetramethyl-1-oxa-4-aza-2,6-disilacyclohexane.

* * * * *

UNITED STATES PATENT AND TRADEMARK OFFICE
CERTIFICATE OF CORRECTION

PATENT NO. : 4,208,408
DATED : June 17, 1980
INVENTOR(S) : Sandor Barcza

It is certified that error appears in the above—identified patent and that said Letters Patent is hereby corrected as shown below:

Column 1, line 6; after "of", delete "copend-".

Column 1, line 7; before "application", delete "ing".

Column 6, lines 32 and 33 (lines 2 and 3 of Claim 15); delete "administering to a mammal in need of said treatment".

Signed and Sealed this

Eighth Day of February 1983

[SEAL]

Attest:

Attesting Officer

GERALD J. MOSSINGHOFF
Commissioner of Patents and Trademarks